United States Patent [19]

Denick, Jr.

[11] Patent Number: 4,717,565

[45] Date of Patent: Jan. 5, 1988

[54] PROCESS FOR THE PREPARATION OF MEDICAMENT ADSORBATES

[75] Inventor: John Denick, Jr., Newton, N.J.

[73] Assignee: Warner-Lambert Company, Morris Plains, N.J.

[21] Appl. No.: 844,901

[22] Filed: Mar. 27, 1986

[51] Int. Cl.⁴ .............................................. A61K 9/18
[52] U.S. Cl. ................................................... 424/155
[58] Field of Search ................................ 424/154, 155

[56] References Cited

U.S. PATENT DOCUMENTS 3,140,978  7/1964  Zentner ................................. 167/55
3,337,402  8/1967  Zentner ................................. 167/55
3,432,593  3/1969  Shepard ................................ 424/20
3,567,819  3/1971  Idson et al. .......................... 424/16
3,636,200  1/1972  Zentner ................................ 424/154
4,029,797  6/1977  Bianculli ............................. 424/260

Primary Examiner—Shep K. Rose
Attorney, Agent, or Firm—Charles A. Gaglia, Jr.; Gary M. Nath

[57] ABSTRACT

A process for preparing a medicament adsorbate by sorbing a medicament drug onto a swollen hydrated complex magnesium aluminum silicate and drying the swollen mass to a final solvent content of up to about 20% by weight of the medicament adsorbate.

18 Claims, No Drawings

PROCESS FOR THE PREPARATION OF MEDICAMENT ADSORBATES

FIELD OF THE INVENTION

This invention relates to a process for preparing a medicament adsorbate which contains a complex magnesium aluminum silicate having sorbed therein a medicament drug.

DESCRIPTION OF THE PRIOR ART

The use of complex magnesium aluminum silicate has been taught in the literature as a method to render bitter drug principles tasteless in liquid, tablet and chewable dosage forms which become bioavailable when the adsorbate reaches the low pH acid media of the stomach.

U.S. Pat. No. 3,337,402 to Zentner discloses the formation of a sedative composition using 7-chloro-1-methyl-5-phenyl-3H-1,4-benzodiazepin-2(1H)-one adsorbed on a complex magnesium aluminum silicate. Zentner notes that when the drug is first dissolved in a lower molecular weight monohydroxy aliphatic alcohol or in an aqueous alcohol mixture and then mixed with a complex magnesium aluminum silicate, the bitter taste and anesthetizing effect on the tongue associated with the drug is reduced or eliminated. Zentner also discloses that the adsorbate may be mixed with other ingredients to form lozenges, tablets, candies, capsules and suspensions.

U.S. Pat. No. 3,567,819 to Idson, et al discloses the formation of a decongestant composition using phenylpropanolamine hydrochloride adsorbed on a complex magnesium aluminum silicate. The objectionable taste of phenylpropanolamine hydrochloride is reduced or eliminated when the drug is first placed in solution and then mixed with complex magnesium aluminum silicate to form an adsorbate. The adsorbate is then dried and used to prepare a chewable multilayered tablet.

SUMMARY OF THE INVENTION

A procedure for preparing a good tasting medicament adsorbate which may contain up to about 35% by weight medicament compound has been unexpectedly discovered.

This has been achieved by sorbing a solution of medicament drug into a hydrated complex magnesium aluminum silicate to form a mass which when dried is an essentially tasteless medicament adsorbate.

DETAILED DESCRIPTION

In particular, it has been found that an essentially tasteless medicament adsorbate is produced by sorbing from about 1% to about 35% by weight of a medicament drug from a solution which has been admixed with a hydrated swollen complex magnesium aluminum silicate sorbent to form a swollen mass. The swollen mass is dried to form an essentially tasteless adsorbate.

While the invention is not to be limited to theoretical considerations, it is believed that the hydration and swelling of complex magnesium aluminum silicate expands the surface area available for adsorbtion and protects the medicament from desorption until the adsorbate is rehydrated and swollen in the digestive system.

Complex magnesium aluminum silicate flakes are actually layers of individual submicron platelets. These platelets are separated by monomolecular water layers. Platelet faces are negatively charged, while the edges have a slight positive charge. When water is added to the complex magnesium aluminum silicate, it penetrates the area between the platelets forcing them apart. The platelets are then separated by layers of water. When fully dispersed in water, the swollen complex magnesium aluminum silicate exists as discrete platelets. The platelets because of their charge form a structure in which the positive platelet edges are attracted to the negative platelet faces. The resulting structure resembles a house of cards in that parallel platelets are connected by perpendicular crosslinking platelets.

In its hydrated state, all of the surface area of the sorbent platelets is available for adsorption. This effectively increases the interstitial sorbent surface area in contact with the medicament drug. The increased surface area results in the formation of adsorbates with a greater degree of taste masking than adsorbates prepared with unhydrated complex magnesium aluminum silicate.

The complex magnesium aluminum silicate may be hydrated prior to addition of the medicament drug or at the same time the drug is added to the sorbent. The medicament drug may be added to the sorbent as a solution or as a solid. If the drug is added as a solid, then the solvent used to hydrate the sorbent must also solubilize the drug. The order of addition of the components of the adsorbate is not critical. The addition may be accomplished by pouring, spraying or related techniques known in the art. It is critical, however, that the resultant mass of sorbent, solvent and medicament drug be mixed thoroughly until uniform. It is also critical that the amount of water in the solvent of the resultant mass be at least about 50% by weight of the solvent. If the amount of water is less than about 50%, the complex magnesium aluminum silicate will not fully hydrate and the adsorbate formed will be less taste masked.

It is believed that the sorbing of the medicament solution into the hydrated swollen complex magnesium aluminum silicate renders the medicament not available for organoleptic taste prior to passage into the digestive tract and subsequent swelling and desorption by the gastric fluid and enzymes. The taste masking sorption effect of this invention is superior to the taste masking found when a medicament drug is adsorbed merely from aqueous, organic or mixed solvents onto a nonhydrated nonswollen complex magnesium aluminum silicate.

In the practice of the present invention, the complex magnesium aluminum silicate is a standard article of commerce, a typical commercial product is known as "Veegum". Veegum is a standard item of commerce and it is sold under that trade name by the R. T. Vanderbuilt Company, Inc., New York, N.Y. Another typical commercial product is known as "Magnabrite". Magnabrite is a standard item of commerce and it is sold under that trade name by the American Colloid Company, Skokie, Ill. The typical average chemical analysis of complex magnesium aluminum silicate, conventionally expressed as oxides, maybe represented as follows:

|  | Percent by Weight | Ratio to Aluminum Oxide |
| --- | --- | --- |
| Silicon dioxide | 55 to 70 | 3.2 to 35 |
| Magnesium oxide | 2.9 to 25 | 0.17 to 12.5 |
| Aluminum oxide | 2.0 to 17 | 1 |
| Ferric oxide | 0.4 to 1.8 |  |
| Calcium oxide | 1.1 to 2.4 |  |

-continued

|  | Percent by Weight | Ratio to Aluminum Oxide |
|---|---|---|
| Sodium oxide | 1.0 to 3.8 |  |
| Potassium oxide | 0.2 to 1.9 |  |
| Ignition Loss | 5.5 to 12.6 |  |

In a preferred embodiment of the invention, the complex magnesium aluminum silicate has the following typical chemical analysis:

|  | Percent by Weight | Ratio to Aluminum Oxide |
|---|---|---|
| Silicon dioxide | 56 to 59 | 14.0 to 29.5 |
| Magnesium oxide | 21 to 24 | 5.2 to 12.0 |
| Aluminum oxide | 2.0 to 4.0 | 1 |
| Ferric oxide | 0.4 to 0.6 |  |
| Calcium oxide | 1.1 to 1.5 |  |
| Sodium oxide | 2.5 to 3.5 |  |
| Potassium oxide | 0.5 to 1.0 |  |
| Ignition Loss | 5.5 to 12.6 |  |

The complex magnesium aluminum silicate of this invention is present in an amount from about 65 to about 99 percent by weight of the final adsorbate complex. In a preferred embodiment, the complex magnesium aluminum silicate is present in an amount of about 70 to about 90 percent by weight of the final adsorbate complex and most preferably from about 75 to about 85 percent.

It has been found that the particle size of the complex magnesium aluminum silicate is not critical in preparing the adsorbates of this invention. While not essential the average particle size of the complex magnesium aluminum silicate may range from about 10 to about 150 microns. Such products have been found suitable to sorb sufficient quantities of the medicament solution to prepare acceptable product.

Any solvent may be used in the inventive process to prepare the adsorbate providing it is capable of dissolving the medicament drug and is miscible with water. Representative solvents include water; lower alcohols, such as methanol, ethanol, propanol, isopropanol, butanol and the like; with water being the preferred solvent.

The medicament drugs used herein may be selected from a wide variety of drugs and their acid addition salts. Neutral compounds as well as organic and inorganic salts may be used provided the drug maintains its medicament value and is soluble in the solvent. Exemplary acid salts include hydrochloride, hydrobromide, orthophosphate, benzoate, maleate, tartrate, succinate, citrate, salicylate, sulfate and acetate.

The weight percent of the drug or its acid addition salt thereof based on the weight of the adsorbate is preferably from about 1% to about 30%, and most preferably about 5% to about 25%, which amounts will vary depending upon the therapeutic dosage permitted.

The medicament drug may be selected from a wide range of unpleasant tasting therapeutic agents and mixtures of therapeutic agents. Nonlimiting illustrative categories and specific examples include:

(a) Analgesics, such as acetaminophen, ibuprofen, phenacetin, and salicylamide;

(b) Antiasmatics, such as aminophylline, metaproterenol, epinephrine, and theophylline;

(c) Antitussives, such as dextromethorphan, dextromethorphan hydrobromide, noscapine, carbetapentane citrate, and chlophedianol hydrochloride;

(d) Antihistamines, such as chlorpheniramine maleate, phenindamine tartrate, pyrilamine maleate, doxylamine succinate, phenyltoloxamine citrate, diphenhydramine hydrochloride, promethazine, and triprolidine;

(e) Antinauseant, such as dimenhydrinate, and meclizine;

(f) Decongestants, such as phenylephrine hydrochloride, phenylpropanolamine hydrochloride, pseudoephedrine hydrochloride, ephedrine;

(g) Various alkaloids, such as codeine phosphate, codeine sulfate and morphine;

(h) Laxatives, such as phenolphthalein, danthron, pamabrom and bisocadyl;

(i) Anti-cholesterolemic and anti-lipid agents such as gemfibrozil;

(j) Appetite suppressants such as phenylpropanolamine hydrochloride, and caffeine;

(k) Central nervous system stimulants such as nicotine;

(l) Expectorants such as guaifenesin;

(m) Anti-inflammatory agents such as isoxicam, meclophenamic acid and naproxen; and (n) Nutritional supplements, including vitamins and minerals, such as niacin, pantothenic acid, vitamin B6, thiamine hydrochloride, riboflavin, potassium iodide, potassium chloride, cupric sulfate, and ferrous sulfate.

Medicaments may be used alone or in combination within the ranges specified above to form the adsorbate.

In a preferred embodiment the medicament is the expectorant guaifenesin.

The medicament adsorbate of the invention is prepared by:

Admixing a complex magnesium aluminum silicate with a medicament drug and a sufficient amount of solvent to dissolve the medicament drug and hydrate the complex magnesium aluminum silicate to form a swollen mass containing said drug in an adsorbed condition, said solvent having a water content of at least about 50% by weight of the solvent, drying the swollen mass to a final solvent content up to about 20% by weight of the medicament adsorbate, and recovering the medicament adsorbate.

In a preferred embodiment, the medicament adsorbate of the invention is prepared by:

(A) preparing a blend by admixing a complex magnesium aluminum silicate with at least an equal weight of solvent to form a swollen complex magnesium aluminum silicate, (B) preparing a solution by dissolving the medicament drug in a solvent.

(C) sorbing the medicament drug within the swollen complex magnesium aluminum silicate by admixing the blend with the solution to form a swollen mass having a homogenous consistency and a water content of at least about 50% by weight of the total solvent content, (D) drying the swollen mass to a final solvent content of up to about 20% by weight of the medicament adsorbate.

(E) recovering the medicament adsorbate.

In another preferred embodiment, the medicament adsorbate of the invention is prepared by:

(A) preparing a solution by dissolving the medicament drug in an amount of solvent at least equal in weight to the amount of complex magnesium aluminum silicate, said solvent having a water content of at least about 50% by weight of the solvent.

(B) sorbing the medicament drug within a complex magnesium aluminum silicate by admixing the solution with the complex magnesium aluminum silicate to form a swollen homogenous mass, and (C) drying the swollen mass to a final solvent content of up to about 20% by weight of the medicament adsorbate.

(D) recovering the medicament adsorbate.

To form the medicament drug solution, the medicament drug is admixed with a solvent until it is dissolved. The solvent may be heated to aid dissolution. Preferably the solvent is heated from about 65° C. to about 99° C.

The amount of solvent utilized to dissolve the medicament drug will vary depending on the solubility of the particular medicament drug used to form the adsorbate. The weight percent of the solvent used to form the solution based on the medicament adsorbate is from about 10% to about 60%, preferably about 15% to about 45%, and most preferably about 20% to about 35% when the adsorbate is formed with swollen hydrated complex magnesium aluminum silicate.

When a complex magnesium aluminum silicate-solvent blend is used in the process the complex magnesium aluminum silicate and solvent are admixed until the silicate is swollen and the mixture is uniform. The solvent may be heated to aid formation of a uniform swollen blend. Preferably the solvent is heated from about 35° C. to about 99° C.

The amount of solvent utilized to prepare the swollen complex magnesium aluminum silicate-solvent blend may vary widely but is generally from about 1 to about 20 times the weight of the complex magnesium aluminum silicate and preferably from about 5 to about 10 times the weight.

When the third procedure, the alternative preferred procedure, described above is utilized, the medicament drug is dissolved in sufficient solvent to hydrate and swell the complex magnesium aluminum silicate sorbent. The amount of solvent utilized may vary widely but is generally from about 1 to about 20 times the weight of complex magnesium aluminum silicate and preferably from about 5 to about 10 times the weight. The solvent must have a water content of at least about 50% by weight of the solvent. A water content of less than about 50% will not sufficiently hydrate and swell the complex magnesium aluminum silicate.

The process involves the step of dissolving the medicament drug in a suitable inert solvent. The resultant solution is then sorbed with mixing for about 5 to about 45 minutes into the swelled complex magnesium aluminum silicate. The resulting product is dried to a predetermined solvent content of up to about 20% and preferably about 2% to about 15% by weight of the medicament adsorbate. Conditions for removing the solvent are not critical. The swelled adsorbate may be heated to aid solvent removal. Preferably the adsorbate is heated from about 60° C. to about 95° C. most preferably from about 65° C. to about 85° C.

The medicament adsorbate once prepared may be stored for future use or formulated with conventional additives, that is pharmaceutically acceptable carriers, to prepare medicated compositions which offer a variety of textures to suit particular applications. Such compositions may be in the form of a lozenge, tablet, toffee, nougat, chewy candy, chewing gum, suspension, and so forth. The pharmaceutically acceptable carriers may be prepared from a wide range of materials. Without being limited thereto, such materials include diluents, binders and adhesives, lubricants, disintegrants, colorants, bulking agents, flavorings, sweeteners and miscellaneous materials such as buffers and adsorbents in order to prepare a particular medicated composition. The preparation of confectionery and chewing gum products is well known and does not constitute an essential aspect of this invention.

As used herein, the term confectionery material means a product containing a bulking agent selected from a wide variety of materials such as sugar, corn syrup, and in the case of sugarless bulking agents, sugar alcohols such as sorbitol and mannitol and mixtures thereof. Confectionery material may include such exemplary substances as lozenges, tablets, toffee, nougat, chewy candy and so forth. In general, the bulking agent will comprise from about 5 to about 99% and preferably 20 to about 95% by weight of the medicated confectionery product.

Lozenges are flavored medicated dosage forms intended to be sucked and held the mouth. They may be in the form of various shapes, the most common being flat, circular, octagonal and biconvex forms. The lozenge bases are generally in two forms, hard, boiled candy lozenges and compressed tablet lozenges.

The hard boiled candy lozenges are prepared from a mixture of sugar and other carbohydrates that are kept in an amorphous or glassy condition. This form can be considered a solid syrup of sugars generally having from 0.5 to about 1.5% moisture. Such materials normally contain up to about 92% corn syrup, up to about 70% sugar and from 0.1% to about 5.0% water. The syrup component generally is prepared from corn syrups high in dextrose, but may include other materials. Further ingredients such as flavorings, sweetener, acidulents, colorants and so forth may also be added.

Boiled candy lozenges may also be prepared from nonfermentable sugars such as sorbitol, mannitol, and hydrogenated corn syrup. The candy lozenges may contain up to about 95% sorbitol, a mixture of sorbitol and mannitol at a ratio of about 9.5 to 0.5 up to about 7.5 to 2.5 and hydrogenated corn syrup up to about 55% of the syrup component.

In contrast, compressed tablet lozenges contain particulate materials and are formed into structures under pressure. They generally contain sugars in amounts up to 95% and typical tablet excipients such as binders and lubricants as well as flavors, colorants and so forth.

The lozenges may be made of soft confectionary materials such as those contained in nougat. These materials contain two primary components, namely a high boiling syrup such as corn syrup or the like, and a relatively light textured frappe, generally prepared from gelatin, egg albumen, milk proteins such as casein, and vegetable proteins such as soy protein, and the like. The frappe is generally relatively light, and may, for example, range in density from about 0.5 to about 0.7g/cc.

By comparison, the high boiling syrup, or "bob syrup," is relatively viscous and possesses a higher density, and frequently contains a substantial amount of sugar. Conventionally, the final nougat composition is prepared by the addition of the "bob syrup" to the frappe under agitation, to form the basic nougat mixture. Further ingredients such as flavorings, oils, additional sugar and the like may be added thereafter also under agitation. A general discussion of the composition and preparation of nougat confections may be found in B. W. Minifie, *CHOCOLATE, COCOA AND CONFECTIONERY:* Science and Technology, 2nd edition, AVI Publishing Co., Inc., Westport, Conn., (1980), at pages 424-425, which disclosure is incorporated herein by reference.

Pharmaceutical suspensions of this invention may be prepared by conventional methods long established in the art of pharmaceutical compounding. Suspensions may contain conventional adjunct material employed in formulating the suspensions of the art. The suspensions of the present invention can comprise:

(a) preservatives such as benzoic acid, sorbic acid, methylparaben, propylparaben and ethylenediaminetetracetic acid (EDTA). Preservatives are generally present in amounts up to about 1% and preferably from about 0.05 to about 0.5% by weight of the suspension;

(b) buffers such as citric acid-sodium citrate, phosphoric acid-sodium phosphate, and acetic acid-sodium acetate in amounts up to about 1% and preferably from about 0.05 to about 0.5% by weight of the suspension;

(c) suspending agents or thickeners such as cellulosics like methylcellulose, carageenans like alginic acid and its derivatives, xanthan gums, gelatin, acacia, and microcrystalline cellulose in amounts up to about 20% and preferably from about 1% to about 15% by weight of the suspension:

(d) antifoaming agents such as dimethyl polysiloxane in amounts up to about 0.2% and preferably from about 0.01 to about 0.1% by weight of the suspension;

(e) sweeteners includes those sweeteners both natural and artificial well known in the art.

Sweetening agents such as monosaccharides, disaccharides and polysaccharides such as xylose, ribose, glucose, mannose, galactose, fructose, dextrose, sucrose, maltose, partially hydrolyzed starch or corn syrup solids and sugar alcohols such as sorbitol, xylitol, mannitol and mixtures thereof may be utilized in amounts from about 10% to about 60% and preferably from about 20% to about 50% by weight of the suspension. Water soluble artificial sweeteners such as saccharin and saccharin salts such as sodium or calcium, cyclamate salts, acesulfame-K, aspartame and the like and mixtures thereof may be utilized in amounts from about 0.001% to about 5% by weight of the suspension;

(f) flavorants include both natural and artificial flavors, and mints such as peppermint, menthol, vanilla, artificial vanilla, chocolate, artificial chocolate, cinnamon, various fruit flavors, both individual and mixed may be utilized in amounts from about 0.5% to about 5% by weight of the suspension;

(g) colorants useful in the present invention include pigments which may be incorporated in amounts of up to about 6% by weight of the composition. A preferred pigment, titanium dioxide, may be incorporated in amounts up to about 1%. Also, the colorants may include other dyes suitable for food, drug and cosmetic applications, and known as F.D.&C. dyes and the like. such dyes are generally presents in amount up to about 0.25% and preferably from about 0.05 to about 0.2% by weight of the suspension;

(h) decolorizing agents such as sodium metabisufite, ascorbic acid and the like may be incorporated into the suspension to prevent color changes due to aging. In general, amounts up to about 0.25% and preferably 0.05 to 0.2% by weight of the suspension are used;

(i) solubilizers such as alcohol, propylene glycol, polyethylene glycol and the like may be used to solubilize the flavors. Solubilizing agents are generally present in amounts up to about 10%; preferably from about 2% to about 5% by weight of the suspension.

Pharmaceutical suspensions of the present invention may be prepared as follows:

(A) admixing the thickener with water heated from about 40° C. to about 95° C. preferably about 40° C. to about 70° C. to form a dispersion if the thickener is not water soluble or a solution if the thickener is water soluble, (B) admix the sweetener with water to form a solution, (C) admix the medicament adsorbate with the thickener-water admixture to form a uniform thickener-adsorbate composition, (D) combine the sweetener solution with the thickener-adsorbate composition and mix until uniform, (E) admix optional ingredients such as colorants, flavors, decolorants, solubilizers, antifoaming agents, buffers and additional water with the mixture of step (D) to form the suspension.

Pharmaceutical tablets of this invention may also be in chewable form. This form is particularly advantageous because of convenience and patient acceptance. To achieve acceptable stability and quality as well as good taste and mouth feel several considerations are important, namely amount of active substance per tablet, flavor, compressibility and organoleptic properties of the drug.

The preparation of chewable medicated candy is by procedures similar to those used to make soft confectionary products. This procedure generally involves the formation of a boiled sugar-corn syrup blend to which is added a frappe mixture. The boiled sugar-corn syrup blend may be prepared from sugar and corn syrup blended in parts by weight ratio of about 90 to 10 to about 10 to 90. This blend is heated to temperatures above 121° C. to remove water and to form a molten mass. The frappe is generally prepared from gelatin, egg albumen, milk proteins such as casein, and vegetable proteins such as soy protein, and the like which are added to a gelatin solution and rapidly mixed at ambient temperature to form an aerated sponge like mass. The frappe is then added to the molten candy base and mixed until homogenous at temperatures between 65° C. and 121° C.

The medicament adsorbate can then be added as the temperature of the mix is lowered to about 65° C. to about 135° C. whereupon additional ingredients are added such as flavors, and colorants. The formulation is further cooled and formed to pieces of desired dimensions.

A general discussion of the lozenge and chewable tablet forms of confectionary may be found in H. A. Lieberman and L. Lachman, *Pharmaceutical Dosage Forms:* Tablets Volume 1, Marcel Dekker, Inc., New York, N.Y. at pages 289 to 466 which disclosure is incorporated herein by reference.

As used herein, the term chewing gum product means a product containing a chewing gum formulation. In general, the chewing gum formulation will comprise from about 5 to about 99% and preferably 20 to about 95% by weight of the medicated chewing gum product.

With regard to a chewing gum formulation, such formulations contain a gum base and various additives, such as sweeteners and flavors. The gum base employed will vary greatly depending on various factors such as the type of base used, consistency desired and other components used to make the final product. In general, amounts of about 5% to about 45% by weight of the final chewing gum composition are acceptable for use in chewing gum compositions with preferred amounts of about 15% to about 25% by weight. The gum base may be any water-insoluble gum base well known in the art. Illustrative examples of suitable polymers in gum bases include both natural and synthetic elastomers and rubbers. For example, those polymers which are suitable in gum bases, include, without limitation, substances of vegetable origin such as chicle, jelutong, gutta percha and crown gum. Synthetic elastomers such as butadienestyrene copolymers, isobutylene-isoprene copolymers, polyethylene, polyisobutyliene and polyvinylacetate and mixtures thereof, are particularly useful.

The gum base composition may contain elastomer solvents to aid in softening the elastomer component. Such elastomer solvents may comprise methyl, glycerol or pentaerythritol esters of rosins or modified rosins, such as hydrogenated, dimerized or polymerized rosins or mixtures thereof. Examples of elastomer solvents suitable for use herein include the pentaerythritol ester of partially hydrogenated wood rosin, pentaerythritol ester of wood rosin, glycerol ester of wood rosin, glycerol ester of partially dimerized rosin, glycerol ester of polymerized rosin, glycerol ester of tall oil rosin, glycerol ester of wood rosin and partially hydrogenated wood rosin and partially hydrogenated methyl ester of rosin, such as polymers of alpha-pinene and beta-pinene; terpene resins including polyterpene and mixtures thereof. The solvent may be employed in an amount ranging from about 10% to about 75% and preferably about 45% to about 70% by weight to the gum base.

A variety of traditional ingredients such as plasticizers or softeners such as lanolin, stearic acid, sodium stearate, potassium stearate, glyceryl triacetate, glycerine and the like as well as natural and synthetic waxes, petroleum waxes, such as polyurethane waxes, paraffin waxes and microcrystalline waxes may also be incorporated into the gum base to obtain a variety of desirable textures and consistency properties. These individual additional materials are generally employed in amounts of up to about 30% by weight and preferably in amounts from about 3% to about 20% by weight of the final gum base composition.

The chewing gum composition may additionally include the conventional additives of flavoring agents, coloring agents such as titanium dioxide, emulsifiers such as lecithin and glyceryl monostearate; and additional fillers such as aluminum hydroxide, alumina, aluminum silicates, calcium carbonate, and talc and combinations thereof. These fillers may also be used in the gum base in various amounts. Preferably the amount of fillers when used will vary from about 4% to about 30% by weight of the final chewing gum.

In the instance where auxiliary sweeteners are utilized, the present invention contemplates the inclusion of those sweeteners well known in the art, including both natural and artificial sweeteners. Thus, additional sweeteners may be chosen from the following non-limiting list:

A. Water-soluble sweetening agents such as monosaccharides, disaccharides and polysaccharides such as xylose, ribose, glucose, mannose, galactose, fructose, dextrose, sucrose, maltose, partially hydrolyzed starch, or corn syrup solids and sugar alcohols such as sorbitol, xylitol, mannitol and mixtures thereof.

B. Water-soluble artificial sweeteners such as the soluble saccharin salts, i.e., sodium, or calcium saccharin salts, cyclamate salts, acesulfame-K and the like, and the free acid form of saccharin.

C. Dipeptide based sweeteners such as L-aspartyl-L-phenylalanine methyl ester and materials described in U.S. Pat. No. 3,492,131 and the like.

In general, the amount of sweetener will vary with the desired amount of sweeteners selected for a particular chewing gum. This amount will normally be 0.001% to about 90% by weight when using an easily extractable sweetener. The water-soluble sweeteners described in category A above, are preferably used in amounts of about 25% to about 75% by weight, and most preferably from about 50% to about 65% by weight of the final chewing gum composition. In contrast, the artificial sweeteners described in categories B and C are used in amounts of about 0.005% to about 5.0% and most preferably about 0.05% to about 2.5% by weight of the final chewing gum composition. These amounts are ordinarily necessary to achieve a desired level of sweetness independent from the flavor level achieved from flavor oils. While water may be added independently with dry sweetners, it will generally be added as part of a corn syrup or corn syrup mixture.

Suitable flavorings include both natural and artificial flavors, and mints such as peppermint, spearmint, menthol, artificial vanilla, vanilla, artificial chocolate, chocolate, cinnamon, various fruit flavors, both individual and mixed, and the like are contemplated. The flavorings are generally utilized in amounts that will vary depending upon the individual flavor, and may, for example, range in amounts of about 0.5% to about 3% by weight of the final composition.

The colorants useful in the present invention, include the pigments which may be incorporated in amounts of up to about 6% by weight of the composition. A preferred pigment, titanium dioxide, may be incorporated in amounts of up to about 1% by weight. Also, the colorants may include other dyes suitable for food, drug and cosmetic applications, and known as F.D. & C. dyes and the like. The materials acceptable for the foregoing spectrum of use are preferably water-soluble. Illustrative examples include the indigo dye, known as F.D. & C. Blue No. 2, which is the disodium salt of 5,5-indigotindisulfonic acid. Similarly, the dye known as F.D. & C. Green No. 1, comprises a triphenylmethane dye and is the monosodium salt of 4-[4-N-ethyl-p-sulfobenzylamino) diphenylmethylene]-[1-(N-ethyl-N-p-sulfoniumbenzyl)-2,5-cyclohexadienimine]. A full recitation of all F.D. & C. and D. & C. colorants and their corresponding chemical structures may be found in the Kirk-Othmer Encyclopedia of Chemical Technology, 3rd edition, in Volume 6, at pages 561–595, which text is accordingly incorporated herein by reference.

Suitable oils and fats that are usable would include partially hydrogenated vegetable or animal fats, such as coconut oil, palm kernel oil, beef tallow, lard, and the like. These ingredients are generally utilized in amounts with respect to the comestible product of up to about 7.0% by weight, and preferably up to about 3.5% by weight of the final product.

It is generally believed that as the required amount of active substance per structure gets smaller and/or less bad tasting, the task at arriving at an acceptable formulation becomes easier due to the greater number of formulations available. Alternatively, extremely bad-tasting and/or high-dose drugs are difficult to formulate into medicament/chewable tablets. The medicament adsorbates of this invention overcome these difficulties.

The quantity of adsorbate used may vary widely depending upon the particular medicament drug dosage. Amounts of medicament of about 1.0 to about 400 mg per medicated dosage are usable dependent upon the particular medicament. Naturally amounts of medicament adsorbate used will vary depending on the therapeutic dosage required and the amount of medicament sorbed on the substrate. Illustrative examples are described below.

The usual dosage of dextromethorphan hydrobromide is between 10 and 30 mg per tablet. Incorporation of the adsorbate into, for example, a candy base is not difficult. It is compatible with most flavors and is stable over a wide pH range. The dextromethorphan HBr when added as the medicament adsorbate avoids its bitter taste and flavoring difficulty.

The usual dosage of phenylpropanolamine hydrochloride is about 12.5 to 25 mg per tablet. The usual dosage of guaifenesin is 100 to 400 mg per tablet. The usual dosage of pseudoephedrine hydrochloride is 15 to 60 mg per tablet. The usual dosage range of chlorpheniramine maleate is 2 to 4 mg and lends itself easily to incorporation into a candy base. Naturally, the exact amount used will vary with the particular application and drug. These formulations are not difficult to flavor because the adsorbates formed with these compounds substantially eliminate medicament after-taste.

The medicament adsorbate is generally present with the pharmaceutically acceptable carrier in an amount of from about 1% to about 60% by weight of the final composition. The exact amount will be dependent upon the particular medicament and dosage required.

The present invention is further illustrated by the following examples. All parts and percentages in the examples and throughout the specification and claims are by total weight of the medicament adsorbate unless otherwise indicated.

The complex magnesium aluminum silicate of Examples 1 and 2 has the following typical chemical analysis:

|  | Percent by Weight | Ratio to Aluminum Oxide |
|---|---|---|
| Silicon dioxide | 56 to 59 | 14.0 to 29.5 |
| Magnesium oxide | 21 to 24 | 5.2 to 12.0 |
| Aluminum oxide | 2.0 to 4.0 | 1 |
| Ferric oxide | 0.4 to 0.6 |  |
| Calcium oxide | 1.1 to 1.5 |  |
| Sodium oxide | 2.5 to 3.5 |  |
| Potassium oxide | 0.5 to 1.0 |  |
| Ignition Loss | 5.5 to 12.6 |  |

EXAMPLE 1

(Inventive Run 1)

This Example demonstrates a method for preparing a quaifenesin adsorbate according to the process of the invention.

To 1200 grams of heated water held at about 85° C. to about 95° C. is mixed 1200 grams of complex magnesium aluminum silicate to form a swollen complex magnesium aluminum silicate. The mixing is continued for about 15 minutes until a uniform swollen mixture results.

To 2000 grams of heated water held at about 85° C. to about 95° C. is mixed 270 grams of guaifenesin until a solution is formed.

The guaifenesin solution is mixed with the water: complex magnesium aluminum silicate mixture until a swollen homogeneous mass is obtained. The swollen mass is then dried at about 75° C. for about 16 hours. The resultant dried mass is then milled to produce a free flowing particulate material having a particle size of about 100 microns.

An organoleptic evaluation test was performed on the product to determine the presence or absence of bitterness.

The adsorbate of this example has significantly less bitterness than comparative Example 2.

EXAMPLE 2

(Non-Inventive Run A)

This Example demonstrates a method for preparing a guaifenesin adsorbate not according to the process of the invention.

To 1500 grams of heated water held at 85° C. is mixed 750 grams of guaifenesin until a solution is formed. The resultant solution is then added with mixing to 3000 grams of complex magnesium aluminum silicate. Mixing is continued 10 minutes until a homogeneous mass is obtained. The mass is then dried at about 75° C. for about 16 hours. The resultant dried mass is then milled to produce a free flowing particulate material having a particle size of about 100 microns.

An organoleptic evaluation test was performed on the product to determine the presence or absence of bitterness.

The adsorbate of this example has an acceptable level of bitterness.

This invention being thus described, it will be obvious that the same may be varied in many ways. Such variations are not to be regarded as a departure from the spirit and scope of the invention and all such modifications are intended to be included within the scope of the following claims.

I claim:

1. A process for preparing a medicament adsorbate which comprises:
admixing a complex magnesium aluminum silicate with a medicament drug and a sufficient amount of solvent to dissolve the medicament drug and hydrate the complex magnesium aluminum silicate to form a swollen mass containing said drug in an adsorbed condition, said solvent having a water content of at least about 50% by weight of the solvent, drying the swollen mass to a final solvent content up to about 20% by weight of the medicament adsorbate, and recovering the medicament adsorbate.

2. The process of claim 1 wherein the solvent is present in an amount from about 1 to about 20 times the weight of the complex magnesium aluminum silicate.

3. The process of claim 1 wherein the swollen mass is dried to a final solvent content of about 2% to about 15% by weight of the medicament adsorbate.

4. The process of claim 1 which comprises: employing about 65% to about 99% by weight of complex magnesium aluminum silicate, and about 1% to about 35% by weight of medicament drug, all percents herein are by weight percent of the medicament adsorbate.

5. The process of claim 1 wherein the complex magnesium aluminum silicate has the following typical chemical analysis:

|  | Percent by Weight | Ratio to Aluminum Oxide |
|---|---|---|
| Silicon dioxide | 55 to 70 | 3.2 to 35 |
| Magnesium oxide | 2.9 to 25 | 0.17 to 12.5 |
| Aluminum oxide | 2.0 to 17 | 1 |
| Ferric oxide | 0.4 to 1.8 |  |
| Calcium oxide | 1.1 to 2.4 |  |
| Sodium oxide | 1.0 to 3.8 |  |
| Potassium oxide | 0.2 to 1.9 |  |
| Ignition Loss | 5.5 to 12.6 |  |

6. The process of claim 1 wherein the complex magnesium aluminum silicate has the following typical chemical analysis:

|  | Percent by Weight | Ratio to Aluminum Oxide |
|---|---|---|
| Silicon dioxide | 56 to 59 | 14.0 to 35 |
| Magnesium oxide | 21 to 24 | 5.2 to 12.0 |
| Aluminum oxide | 2.0 to 4.0 | 1 |
| Ferric oxide | 0.4 to 0.6 |  |
| Calcium oxide | 1.1 to 1.5 |  |
| Sodium oxide | 2.5 to 3.5 |  |
| Potassium oxide | 0.5 to 1.0 |  |
| Ignition Loss | 5.5 to 12.6 |  |

7. The process for preparing a medicament adsorbate which comprises:
   (A) preparing a blend by admixing a complex magnesium aluminum silicate with at least an equal weight of solvent to form a swollen complex magnesium aluminum silicate,
   (B) preparing a solution by dissolving the medicament drug in a solvent,
   (C) sorbing the medicament drug within the swollen complex magnesium aluminum silicate by admixing the blend with the solution to form a swollen mass having a homogenous consistency and a water content of at least about 50% by weight of the total solvent content,
   (D) drying the swollen mass to a final solvent content of up to about 20% by weight of the medicament adsorbate,
   (E) recovering the medicament adsorbate.

8. The process of claim 7 wherein the complex magnesium aluminum silicate has the following typical chemical analysis:

|  | Percent by Weight | Ratio to Aluminum Oxide |
|---|---|---|
| Silicon dioxide | 55 to 70 | 3.2 to 35 |
| Magnesium oxide | 2.9 to 25 | 0.17 to 12.5 |
| Aluminum oxide | 2.0 to 17 | 1 |
| Ferric oxide | 0.4 to 1.8 |  |
| Calcium oxide | 1.1 to 2.4 |  |
| Sodium oxide | 1.0 to 3.8 |  |
| Potassium oxide | 0.2 to 1.9 |  |
| Ignition Loss | 5.5 to 12.6 |  |

9. The process of claim 7 wherein the complex magnesium aluminum silicate has the following typical chemical analysis:

|  | Percent by Weight | Ratio to Aluminum Oxide |
|---|---|---|
| Silicon dioxide | 56 to 59 | 14.0 to 35 |
| Magnesium oxide | 21 to 24 | 5.2 to 12.0 |
| Aluminum oxide | 2.0 to 4.0 | 1 |
| Ferric oxide | 0.4 to 0.6 |  |
| Calcium oxide | 1.1 to 1.5 |  |
| Sodium oxide | 2.5 to 3.5 |  |
| Potassium oxide | 0.5 to 1.0 |  |
| Ignition Loss | 5.5 to 12.6 |  |

10. The process of claim 7 which comprises preparing the solution with solvent in an amount from about 10% to about 60% by weight of the complex magnesium aluminum silicate, and preparing the blend with solvent in an amount from about 1 to about 20 times the weight of the complex magnesium aluminum silicate.

11. The process of claim 7 wherein the swollen mass is dried to a final solvent content of about 2% to about 15% by weight of the medicament adsorbate.

12. The process for claim 7 which comprises: employing about 65% to about 99% by weight of complex magnesium aluminum silicate, and about 1% to about 35% by weight of medicament drug, all percents herein are by weight percent of the medicament adsorbate.

13. A process for preparing a medicament adsorbate which comprises:
    (A) preparing a solution by dissolving a medicament drug in an amount of solvent at least equal in weight to the amount of complex magnesium aluminum silicate said solvent having a water content of at least about 50% by weight of the solvent,
    (B) sorbing the medicament drug within a complex magnesium aluminum silicate by admixing the solution with the complex magnesium aluminum silicate to form a swollen homogenous mass, and
    (C) drying the swollen mass to a final solvent content of up to about 20% by weight of the medicament adsorbate,
    (D) recovering the swollen medicament adsorbate.

14. The process of claim 13 wherein the swollen mass is dried to a final solvent content of about 2% to about 20% by weight of the medicament adsorbate.

15. The process of claim 13 which comprises: employing about 65% to about 99% by weight of complex magnesium aluminum silicate, about 1% to about 35% by weight of medicament drug, about 0.05% to about 4% by weight of surfactant, all percents herein are by weight percent of the medicament adsorbate.

16. The process of claim 13 wherein the complex magnesium aluminum silicate has the following typical chemical analysis:

|  | Percent by Weight | Ratio to Aluminum Oxide |
|---|---|---|
| Silicon dioxide | 55 to 70 | 3.2 to 35 |
| Magnesium oxide | 2.9 to 25 | 0.17 to 12.5 |
| Aluminum oxide | 2.0 to 17 | 1 |
| Ferric oxide | 0.4 to 1.8 |  |
| Calcium oxide | 1.1 to 2.4 |  |
| Sodium oxide | 1.0 to 3.8 |  |
| Potassium oxide | 0.2 to 1.9 |  |
| Ignition Loss | 5.5 to 12.6 |  |

17. The process of claim 13 wherein the complex magnesium aluminum silicate has the following typical chemical analysis:

|  | Percent by Weight | Ratio to Aluminum Oxide |
|---|---|---|
| Silicon dioxide | 56 to 59 | 14.0 to 35 |
| Magnesium oxide | 21 to 24 | 5.2 to 12.0 |
| Aluminum oxide | 2.0 to 4.0 | 1 |
| Ferric oxide | 0.4 to 0.6 | |
| Calcium oxide | 1.1 to 1.5 | |
| Sodium oxide | 2.5 to 3.5 | |
| Potassium oxide | 0.5 to 1.0 | |
| Ingition Loss | 5.5 to 12.6 | |

18. The process of claim 13 wherein the solvent is present in an amount from about 1 to about 20 times the weight of the complex magnesium aluminum silicate.

* * * * *